US00PP35201P3

(12) United States Plant Patent
Olesen

(10) Patent No.: US PP35,201 P3
(45) Date of Patent: Jun. 6, 2023

(54) ROSE PLANT NAMED 'POULPAL094'

(50) Latin Name: *Rosa hybrida*
Varietal Denomination: Poulpal094

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/803,614

(22) Filed: Sep. 13, 2022

(65) Prior Publication Data

US 2023/0103291 P1 Mar. 30, 2023

(30) Foreign Application Priority Data

Sep. 24, 2021 (QZ) ..... PBR 2021/2361

(51) Int. Cl.
*A01H 5/02* (2018.01)
*A01H 6/74* (2018.01)

(52) U.S. Cl.
USPC ..... Plt./146

(58) Field of Classification Search
USPC ..... Plt./101, 141, 146
See application file for complete search history.

(56) References Cited

PUBLICATIONS

Poulsen Roser A/S website. 2022. citation for 'Hatfield', https://www.poulsenroser.dk/en/roses/ShowProduct/63000. 2 pages. (Year: 2022).*

* cited by examiner

*Primary Examiner* — Karen M Redden

(57) ABSTRACT

A new garden rose plant of the Compact Floribunda class which has abundant, orange flowers and attractive foliage. This new and distinct variety has shown to be uniform and stable in the resulting generations from asexual propagation.

1 Drawing Sheet

Botanical designation: *Rosa hybrida.*
Variety denomination: 'Poulpal094'.

This application claims priority to Plant Breeder's Rights Application Number 2021/2361, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpal094', originated as a single seedling from the stated cross.

The new variety may be distinguished from its male pollen parent and female seed parent primarily by the following characteristics. The male pollen parent plant has growth height of 25 cm while the new variety has a growth height of 30 to 55 cm. The male pollen parent also has near white flowers, while the claimed plant has orange flowers. The female seed parent plant has red flowers while the new variety has orange flowers.

The objective of the hybridization of this rose variety was to create a new and distinct variety with unique qualities, such as:

1. Uniform and abundant orange flowers;
2. Vigorous, but compact growth when propagated on its own roots;
3. Exceptional disease resistance.

This combination of qualities is not present in previously available commercial cultivars of this type, known to the inventor, and distinguish 'Poulpal094' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpal094' was selected in the spring of 2012 by the inventor as a single plant from the progeny of the aforementioned hybridization.

Asexual reproduction of 'Poulpal094' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpal094' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpal094'. Specifically illustrated in the drawing are fully mature open flowers viewed from above and the side, sepals detached showing strong foliaceous appendages, petals detached revealing reproductive flower parts flower buds upon opening, juvenile stem and leaves, and a mature leaf. Plants shown are 2 years of age.

DETAILED DESCRIPTION OF THE VARIETY

The following is a description of 'Poulpal094', as observed in its growth in a glass house located in Odense Denmark. Observed plants are 6 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulpal080', U.S. Plant Pat. No. 32,298 are compared to 'Poulpal094'. The claimed plant has a general tonality of flower colour of Orange-Red Group 32B and Yellow-Orange Group 19A, becoming Orange Group 29B and Yellow-Orange Group 19A after fully mature. The comparison variety has a general flower tonality of Yellow-Orange Group 16B. While the comparison variety has 35 flower petals, the new variety has about 56 flower petals. While the claimed plant has strong flower perfume, 'Poulpal080' has moderate floral perfume.

FLOWER AND FLOWER BUD

Blooming habit: Continuous.

Flower bud:

- *Size.*—Upon opening, 26 mm in length from base of receptacle to end of bud. Bud diameter is 14 mm.
- *Bud form.*—Globose.
- *Bud color.*—As sepals divide petals are Yellow Group 13C with other intonations of Red Group 41B.
- *Sepal inner surface.*—Color: Yellow-Green Group 147A. Surface: Lightly pubescent.
- *Sepal outer surface.*—Color: Yellow-Green Group 146A, and Yellow-Green Group 144A. Texture: Smooth.
- *Sepal shape.*—Apex: Cirrhose. Base: Flat at union with receptacle.
- *Sepal margin.*—Margins have strong foliaceous appendages on three of the five sepals.
- *Sepal size.*—30 to 50 mm long, 8 to 25 mm wide.
- *Receptacle.*—Texture: Smooth. Size: 5 mm in height, 8 mm wide. Color: Yellow-Green Group 144A. Shape: Funnel.
- *Pedicel.*—Surface: Smooth. Length: About 85 mm. Diameter: 3 to 4 mm on average. Color: Yellow-Green Group 144A. Strength: Strong.
- *Peduncle.*—Length: 5 to 9 to cm. Diameter: About 3 mm. Color: Yellow-Green Group 144A. Texture: Smooth.

Flower bud development: Flower buds are borne in clusters of 3 or single.

Flower bloom:

- *Fragrance.*—Strong perfume.
- *Duration.*—The blooms have a duration on the plant of approximately 19 days. Petals fall cleanly away from plant after flowers have fully matured.
- *Size.*—Flower diameter is 60 mm when open. Flower depth is 30 mm.
- *Flower shape.*—Rosette, very double flower with many slightly overlapping petals of different sizes.
- *Shape of flower, side view.*—The upper portion is convex. The lower portion is deep concave.

Petalage: Under normal conditions, flowers have about 56 petals.

General tonality of flower: Open flowers are Orange-Red Group 32B and Yellow-Orange Group 19A. Becoming Orange Group 29B and Yellow-Orange Group 19A after fully mature.

Petal color:

- *Upon opening, outer petals.*—Upper surface: Basal zone Yellow-Orange Group 14A. Middle zone Yellow-Orange Group 18A. Marginal splashes of Orange-Red Group 33B and Red Group 42B. Lower surface: Basal zone Yellow Group 12B. Yellow Group 14C. Marginal shades of Orange-Red Group 32B.
- *After opening, outer and inner petals.*—Upper surface: Basal zone Yellow Group 7B. Middle and marginal zone Yellow-Orange Group 18A, splashed with Orange-Red Group 33C. Lower surface: Basal zone Yellow Group 12B. Yellow Group 14C. Marginal shades of Orange-Red Group 32B.

Petals:

- *Petal reflex.*—Strong, bilateral.
- *Margin.*—Entire and uniform. Moderate undulations.
- *Shape.*—Broad and elliptic. Apex shape: Rounded. Base shape: Acute.
- *Size.*—25 mm (l)×25 mm (w).
- *Texture.*—Smooth.
- *Thickness.*—Average.

Petaloids:

- *Size.*—20 mm (l) by 9 mm (w).
- *Quantity.*—About 10.
- *Shape.*—Elliptical with an acute base and rounded apex.
- *Color.*—On the upper petaloid surface Middle and marginal zone Yellow-Orange Group 18A, splashed with Orange-Red Group 33C. Basal zone Yellow Group 7B. On the lower surface Yellow Group 14C with marginal intonations of Orange-Red Group 32B. Basal zone Yellow Group 12B.

Reproductive flower parts:

- *Pollen.*—None observed.
- *Anthers.*—Size: 1 mm in length. Color: Greyed-Orange Group N167B. Quantity: 48 on average.
- *Filaments.*—Color: Yellow-Orange Group 23A. Length: 10 mm.
- *Pistils.*—Length: 11 to 12 mm. Quantity: 30 on average.
- *Stigmas.*—Color: Yellow-Green Group 154C.
- *Styles.*—Color: Yellow-Green Group 154C.
- *Location of stigmas.*—Superior in location relative to the length of the filaments and the height of the anthers.
- *Hips.*—None Observed.

PLANT

Plant growth: Upright. Plants are 30 to 55 cm in height, and 30 cm wide.

Stems:

- *Color of juvenile growth.*—Yellow-Green Group 144B.
- *Color of mature growth.*—Yellow-Green Group 146A.
- *Length.*—Canes are about 25 to 35 cm from the base of the plant to the flowering portion.
- *Diameter.*—About 4 mm.

*Internodes*.—On mature canes about 34 mm between nodes.

*Surface texture*.—Young wood: Smooth. Older wood: Smooth.

Long prickles: None observed.

Plant foliage:

*Compound leaf*.—122 mm (l)×90 (w).

*Quantity*.—2 leaves per 10 cm of stem on average.

*Leaf bearing angle to the stem*.—45 degrees.

*Color of juvenile foliage*.—Upper side: Yellow-Green Group 144A with intonations of Greyed-Red Group 178A. Lower side: Yellow-Green Group 144A with intonations of Greyed-Red Group 178A.

*Color of mature foliage*.—Upper side: Yellow-Green Group 147A. Lower side: Yellow-Green Group 147B.

Plant leaves and leaflets:

*Stipules*.—Size: 18 mm long, 2 mm wide. Quantity: 2 per compound leaf. Shape: Linear, slightly broad based with outward extending apices. Margins: Finely serrated. Color:

*Petiole*.—Length: 21 mm. Diameter: 2 mm. Upper surface color: Yellow-Green Group 144A. Lower surface color: Yellow-Green Group 144B.

*Rachis*.—Length: 35 mm. Upper surface color: Yellow-Green Group 144A. Lower surface color: Yellow-Green Group 144B.

*Leaflet*.—Quantity: Normally 5 leaflets. Margins: Serrated. Size: Terminal leaflets are about 57 mm long, 41 mm wide. Shape: Generally elliptical. Base: Rounded. Apex: Acute. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpal094' substantially as described and illustrated herein.

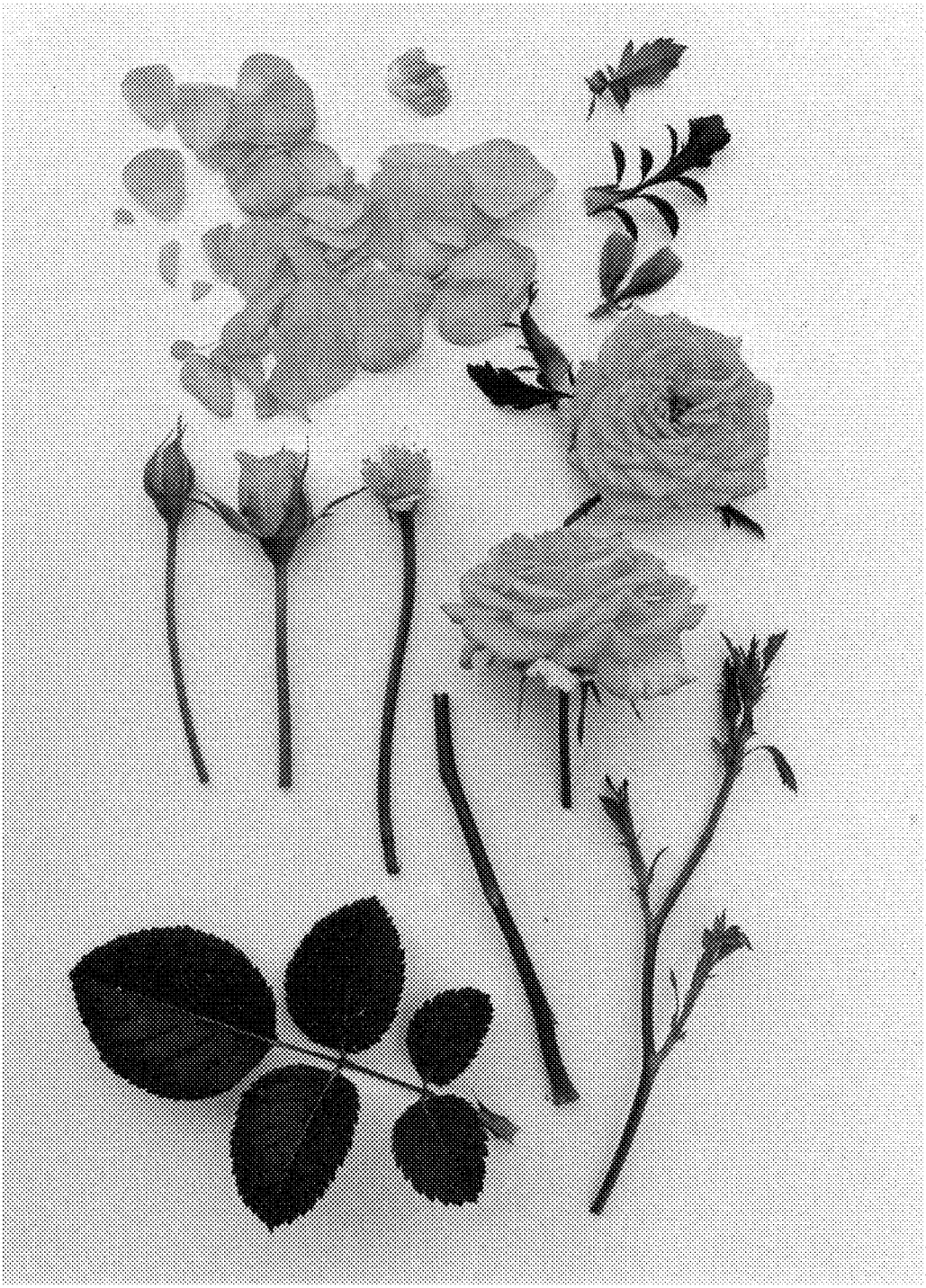

* * * * *